United States Patent
Beister et al.

(10) Patent No.: US 11,116,468 B2
(45) Date of Patent: Sep. 14, 2021

(54) METHOD AND SYSTEM FOR CONTROLLING AN X-RAY PROJECTION IMAGING DEVICE

(71) Applicant: Siemens Healthcare GmbH, Erlangen (DE)

(72) Inventors: Marcel Beister, Erlangen (DE); Ruediger Bock, Langenzenn (DE); Bernhard Geiger, Buckenhof (DE); Sandra Jedinger, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 149 days.

(21) Appl. No.: 16/654,176

(22) Filed: Oct. 16, 2019

(65) Prior Publication Data

US 2020/0121275 A1 Apr. 23, 2020

(30) Foreign Application Priority Data

Oct. 22, 2018 (EP) .................................... 18201824
Mar. 11, 2019 (EP) .................................... 19161868

(51) Int. Cl.
*A61B 5/00* (2006.01)
*A61B 6/00* (2006.01)

(52) U.S. Cl.
CPC .............. *A61B 6/545* (2013.01); *A61B 6/463* (2013.01); *A61B 6/487* (2013.01); *A61B 6/5205* (2013.01); *A61B 6/563* (2013.01)

(58) Field of Classification Search
CPC ......... A61B 6/545; A61B 6/487; A61B 6/563; A61B 6/463; A61B 6/5205; A61B 6/032; A61B 6/025; A61B 2090/376; A61B 2090/3762; A61B 6/542; A61B 6/5217; G06T 7/0012; G06T 2207/10116; G06T 2207/10081; G06T 2207/10072; G06T 11/003; G06T 2207/10121; G06T 2211/40
See application file for complete search history.

(56) References Cited

U.S. PATENT DOCUMENTS

| | | | |
|---|---|---|---|
| 4,924,487 A | 5/1990 | Nishiki | |
| 2010/0128955 A1 | 5/2010 | Walimbe et al. | |
| 2012/0177178 A1 | 7/2012 | Areste et al. | |
| 2019/0374189 A1* | 12/2019 | Kiely | .................. A61B 5/0205 |

FOREIGN PATENT DOCUMENTS

JP 2016171921 A 9/2016

OTHER PUBLICATIONS

Extended European Search Report dated Oct. 21, 2019.

* cited by examiner

*Primary Examiner* — Don K Wong
(74) *Attorney, Agent, or Firm* — Harness, Dickey & Pierce, P.L.C.

(57) ABSTRACT

A method for controlling an X-ray projection imaging device includes applying preferences for a serial radiography image acquisition to the X-ray projection imaging device. The method further includes executing the serial radiography image acquisition with the X-ray projection imaging device; recording data frames at different times during the serial radiography image acquisition; applying a trigger signal to the X-ray projection imaging device during the serial radiography image acquisition; and generating a snapshot image from a subset of the data frames, wherein the subset is chosen from the data frames recorded based on the trigger signal. A related system, a related control unit and a related X-ray projection imaging system are also disclosed.

25 Claims, 2 Drawing Sheets

METHOD AND SYSTEM FOR CONTROLLING AN X-RAY PROJECTION IMAGING DEVICE

PRIORITY STATEMENT

The present application hereby claims priority under 35 U.S.C. § 119 to European patent application numbers EP18201824.2 filed Oct. 22, 2018 and EP19161868.5 filed Mar. 11, 2019, the entire contents of each of which are hereby incorporated herein by reference.

FIELD

Embodiments of the invention generally relate to a method and a system and a control unit for controlling an X-ray projection imaging device in the technical field of serial radiography, especially fluoroscopy, as well as an X-ray projection imaging system.

Especially, embodiments of the invention relate to a method and system for a snapshot mode for digital fluoroscopy.

Embodiments of the invention further generally relate to a computer program, which performs the steps of an embodiment of the inventive method, upon the computer program being executed on a computer; and to an electronically readable storage medium, on which such a computer program is stored.

BACKGROUND

Serial radiography is an imaging technique that uses X-rays to obtain a set of images taken during a certain time period. In its primary application of medical imaging, serial radiography allows a user to image e.g. the internal structure and function of a patient, so that internal procedures can be watched. This is useful for both diagnosis and therapy in many fields of radiology. With fluoroscopy, a special serial radiography method, it is e.g. possible to realize real-time moving images of the interior of an object. In the following, the method of fluoroscopy is used as general example for serial radiography. The term "Digital Fluoroscopy Radiography" (DFR) is used as a superordinate concept for this type and set of operation modes.

In its simplest form, an X-ray projection imaging system suitable for serial radiography comprises an X-ray source and an X-ray detector, between which a patient is placed. This X-ray detector is triggered to produce a set of images at different times during the measuring time period.

During the serial radiography measurement, it is often required to take different images for controlling certain circumstances. For example, during fluoroscopy, the operator could like to document relevant situations, like the status during a procedure, a specific anatomical structure or position of a device, e.g. catheter or port by manually triggering an image. These different images are called "spot images" and differ from the images taken in the course of a serial radiography measurement.

Established methods introduce an interruption of the serial image acquisition, e.g. a fluoroscopy run, for the generation of an intermediate documentation image ("spot image") by using a different operation mode of the X-ray detector and/or the X-ray generator. This makes it very difficult for the operator to capture the desired event without disturbance of the workflow of the serial radiography (fluoroscopy) controlled procedure due to (i) a delayed response of the operator and (ii) the technically limited switching time between operation modes.

To document fluoroscopic procedures, two options are established:
(i) Storing the entire fluoroscopy run to hard disk;
(ii) Perform spot images by interrupting the fluoroscopy run to trigger single exposures stored as separate images for review after the procedure.

To perform the spot images, the X-ray detector commonly has to switch the internal mode to provide a higher quality image with adapted exposure parameters. Stored fluoroscopy run and a single spot image can be archived in a Picture Archiving and Communication System (PACS).

In FIG. 1, the time of interruption of a fluoroscopy acquisition is outlined by using two common examples. Shown is a timeline t where time periods for actions are represented as boxes. The top line of boxes represents a radiographic single image acquisition (RAD), the middle line of boxes a single shot based on serial radiography but limited to one frame (DFR single) and the lower line of boxes the actions to return to fluoroscopy mode.

Regarding the RAD acquisition, the preparation for the RAD-shot R1, the X-ray window XD readout R2 (i.e. the time frame when the X-ray detector is sensitive for radiation) and the processing of the RAD image R3 together with the restart of the fluoroscopy F1 and the X ray window to process a fluoroscopy image F2 results in a time TR over several seconds (depending on technical performance limitations of the devices and user interaction). Since the last fluoroscopy image is displayed before the beginning of the RAD acquisition, there is a relevant time gap until the next fluoroscopy image can be displayed.

Regarding the DFR single acquisition, the preparation for the DFR single shot D1, the X-ray window XD readout D2 and the processing of the DFR image D3 together with the restart of the fluoroscopy F1 and the X ray window to process a fluoroscopy image F2 results in a time TD over several seconds (depending on technical performance limitations of the devices and user interaction). Since the last fluoroscopy image is displayed before the beginning of the DFR single acquisition, there is a shorter (as in RAD mode), but still relevant time gap until the next fluoroscopy image can be displayed.

SUMMARY

At least one embodiment of the present application is directed to improving upon the known systems, devices and methods to facilitate an improvement in controlling an X-ray projection imaging device, especially for providing a snapshot image from fluoroscopy images.

Embodiments of the present application are directed to a method, a system, a control unit and an X-ray projection imaging system.

A method according to at least one embodiment of the present application for controlling an X-ray projection imaging device, comprises:
  applying preferences for a fluoroscopy image acquisition to the X-ray projection imaging device;
  executing the serial radiography image acquisition with the X-ray projection imaging device,
  recording data frames at different times during the serial radiography image acquisition,
  applying a trigger signal to the X-ray projection imaging device during the fluoroscopy image acquisition; and generating a snapshot image from a subset of the recorded fluoroscopy frames, wherein this data frame subset is chosen from the recorded fluoroscopy frames based on the trigger signal.

A system according to an embodiment of the invention for controlling an X-ray projection imaging device, comprises:

a data interface designed for applying preferences for a serial radiography image acquisition to the X-ray projection imaging device;

a data interface designed for starting an execution of a serial radiography image acquisition with the X-ray projection imaging device;

a data interface designed for receiving a number of data frames recorded at different times during the serial radiography image acquisition;

a data interface designed for applying a trigger signal T to the X-ray projection imaging device during the serial radiography image acquisition; and an image-generation unit designed for generating a snapshot image from a subset of the data frames, wherein this data frame subset is chosen from the recorded data frames based on the trigger signal.

A system according to an embodiment of the invention for controlling an X-ray projection imaging device, comprises:

a data interface, designed to apply preferences for a serial radiography image acquisition to the X-ray projection imaging device, start an execution of a serial radiography image acquisition with the X-ray projection imaging device, receive a number of data frames recorded at different times during the serial radiography image acquisition, and apply a trigger signal to the X-ray projection imaging device during the serial radiography image acquisition; and an image-generation unit, designed to generate a snapshot image from a subset of the data frames, wherein the subset being chosen from the data frames recorded based on the trigger signal.

A control unit according to an embodiment of the present application for controlling an X-ray projection imaging device comprises a system according to an embodiment of the present application.

An X-ray projection imaging system according to an embodiment of the present application comprises an X-ray projection imaging device and a control unit according to an embodiment of the present application. Thus, an embodiment of the present application also relates to a medical imaging system (X-ray projection imaging device), such as a radiography or fluoroscopy system (or device), which preferably includes a central processing unit or a computer for the evaluation of image data, wherein a method according to an embodiment of the present application is preferably implemented on the central processing unit or the computer of the medical imaging system.

An embodiment of the present application is also achieved by a non-transitory computer program product storing a computer program that is directly loadable into the memory of a device of a system or a control unit of an X-ray imaging device, and which comprises program units to perform the steps of an embodiment of the method when the program is executed by the control unit or the device. In addition to the computer program, such a computer program product can also comprise further parts such as documentation and/or additional components, also hardware components such as a hardware key (dongle etc.) to facilitate access to the software.

Thus, an embodiment of the present application further provides a non-transitory computer program product storing program elements that can be read and executed by a computer unit in order to perform steps of a method according to an embodiment of the present application when the program elements are executed by the computer unit.

A non-transitory computer readable medium such as a memory stick, a hard-disk or other transportable or permanently-installed carrier can serve to transport and/or to store the executable parts of the computer program product so that these can be read from a processor unit of a control unit or a device. A processor unit can comprise one or more microprocessors or their equivalents.

Thus, an embodiment of the present application further provides a computer-readable medium on which are stored program elements that can be read and executed by a computer unit in order to perform steps of a method according to an embodiment of the present application when the program elements are executed by the computer unit. Further there is provided an electronically readable storage medium, on which a computer program as described above is stored.

BRIEF DESCRIPTION OF DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

In the diagrams, like numbers refer to like objects throughout. Objects in the diagrams are not necessarily drawn to scale.

DETAILED DESCRIPTION OF THE EXAMPLE EMBODIMENTS

Figure 1:
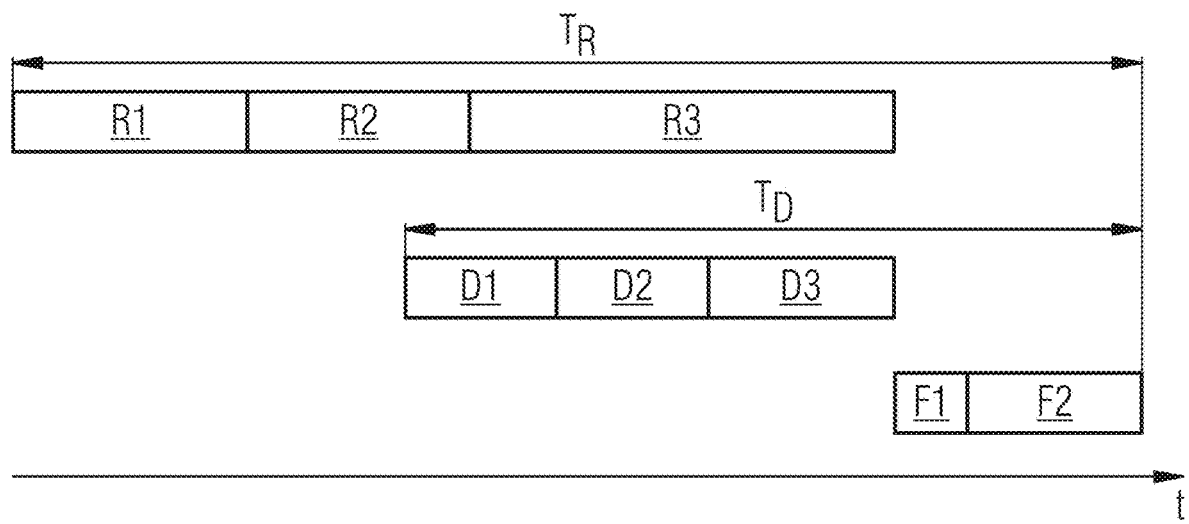
FIG. 1 shows the time of interruption of a fluoroscopy acquisition for a spot image.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices.

The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Nonlimiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A method according to at least one embodiment of the present application for controlling an X-ray projection imaging device, comprises:

applying preferences for a serial radiography image acquisition to the X-ray projection imaging device, wherein "serial radiography" here means the recording of a series of x-ray images. This X-ray projection imaging device is typically designed for capturing a series of consecutive images, e.g. could a fluoroscopy device be used as a suitable X-ray projection imaging device.

In an embodiment, the method further includes executing the serial radiography image acquisition with the X-ray projection imaging device.

In an embodiment, the method further includes recording (a plurality of) data frames at different times during the serial radiography image acquisition. Here a series of X-ray projection images are recorded in form of data frames. Preferably, each data frame represents one image, however, it could also be the case that a data frame is only a part of a picture or represents a group of pictures. It is preferred that the X-ray projection imaging system comprises a digital imaging sensor that records digital images as (digital) data frames.

In an embodiment, the method further includes applying a trigger signal to the X-ray projection imaging device (e.g. by an operator) during the serial radiography image acquisition. This trigger signal may be a manual input by an operator (e.g. by pushing a button) and/or it may be automatically generated (e.g. as a periodic trigger signal).

In an embodiment, the method further includes generating a snapshot image from a subset of the data frames, wherein this data frame subset is chosen from the recorded data frames. Thus, the trigger signal defines the time, where a snapshot image should be generated and this snapshot image is then generated by using two or more data frames (subset) that are chosen based on the time the trigger signal has been applied. It is clear that these data frames for snapshot generation are recorded at different times.

As indicated above, the term "snapshot" is used for an image different from the images (each data frame) recorded in the course of a serial radiography measurement. The snapshot is always generated from several (two or more) data frames recorded at different times. Especially, the snapshot image is considered as an additional image type besides a single spot image, fluoroscopy image or a fluoroscopy scene. Regarding a spot image, this spot image in the state of the art is always recorded by leaving the fluoroscopy mode, recording the spot image and returning to fluoroscopy mode again. The snapshot of the present invention is generated by using recorded information (data frames) while not leaving the serial radiography measurement mode, e.g. the fluoroscopy measurement mode. The snapshot images typically exhibit a lower noise level as they accumulate more dose to one image compared to a single data (fluoroscopy) frame in particular if the dose and/or frame rate is increased during snapshot image generation.

In general terms, an embodiment of the invention relates to a snapshot mode for digital serial X-ray image acquisition, e.g. fluoroscopy. During serial X-ray image acquisition (e.g. fluoroscopy), a snapshot image (could be also designated as a "synthetic" spot image) can be triggered e.g. by the operator. After this trigger a number of subsequent data frames (e.g. fluoroscopy frames) is processed (e.g. by averaging) to a so called snapshot image. The X-ray detector and the X-ray generator are remaining in their original internal mode (no mode switch is performed). With the invention, this can be done with a significantly reduced delay and without interruption of the workflow, but with an improved image quality compared to a single fluoroscopy image.

Normally, the acquisition of intermediate spot images during fluoroscopy requires the X-ray detector (XD) and generator to switch their internal modes. This takes time. When generating a snapshot image according to the invention, the XD and the generator remain in the original fluoroscopy mode. No time consuming mode switch is necessary. Thus, the generation of the snapshot image can be started immediately. This is an advantage of the invention. Thus, it should be noted that the X-ray projection imaging device stays in the mode for serial radiography image acquisition, preferably in the mode for fluoroscopy image acquisition, typically for the whole acquisition. In contrast to the state of the art, it is not necessary to change the acquisition mode in order to provide the snapshot image.

The snapshot images can be used to store relevant situations during a serial radiography measurement (e.g. fluoroscopy) in a separate series and to be sent to PACS for archiving.

The generated snapshot image can be differently marked and post-processed than the normal data (e.g. fluoroscopy) frames and can also be stored separately in e.g. a separate patient series.

A system according to an embodiment of the invention for controlling an X-ray projection imaging device, comprises:

a data interface designed for applying preferences for a serial radiography image acquisition to the X-ray projection imaging device. This data interface may be connected to an input unit, where an operator is able to manually input a trigger signal (e.g. by pushing a button) and/or it may be connected with a trigger generator that is designed to automatically generate a trigger signal (e.g. a periodic trigger signal). The data interface is typically designed to communicate with a part of an X-ray projection imaging device where the preferences are defined and to apply the preferences to this part. Preferably, this component is part of a X-ray projection imaging device that is suitably designed.

In an embodiment, the system further includes a data interface designed for starting an execution of a serial radiography image acquisition with the X-ray projection imaging device. Preferably, this component is part of a X-ray projection imaging device that is suitably designed. It is preferred that this data interface is connected to or identical with the data interface designed for applying preferences.

In an embodiment, the system further includes a data interface designed for receiving a number of data frames recorded at different times during the serial radiography image acquisition. It is preferred that this data interface is connected to or identical with the data interface designed for applying preferences and/or the data interface designed for starting an execution. By using an input/output data interface, data can be sent to an X-ray projection imaging device (preferences and execution signal) and received from the X-ray projection imaging device (data frames).

In an embodiment, the system further includes a data interface designed for applying a trigger signal to the X-ray projection imaging device during the serial radiography image acquisition. Here, also the same or an identical data interface as described above could be used. Especially a data interface designed to send an execution start signal is also able to send a trigger signal.

In an embodiment, the system further includes an image-generation unit designed for generating a snapshot image from a subset of the data frames, wherein this data frame subset is chosen from the recorded data frames based on the trigger signal. The image generation unit is preferably a computing unit that is designed for calculating a snapshot image from the data frame subset, especially by a linear combination of data frames using weighting coefficients for each data frame.

A control unit according to an embodiment of the present application for controlling an X-ray projection imaging device comprises a system according to an embodiment of the present application.

An X-ray projection imaging system according to an embodiment of the present application comprises an X-ray projection imaging device and a control unit according to an embodiment of the present application. Thus, an embodiment of the present application also relates to a medical imaging system (X-ray projection imaging device), such as a radiography or fluoroscopy system (or device), which preferably includes a central processing unit or a computer for the evaluation of image data, wherein a method according to an embodiment of the present application is preferably implemented on the central processing unit or the computer of the medical imaging system.

Some units or modules of the device or the control unit mentioned above can be completely or partially realized as soft-ware modules running on a processor of a system or a control unit. A realization largely in the form of software modules can have the advantage that applications already installed on an existing system can be updated, with relatively little effort, to install and run these units of the present application.

An embodiment of the present application is also achieved by a computer program product with a computer program that is directly loadable into the memory of a device of a system or a control unit of an X-ray imaging device, and which comprises program units to perform the steps of an embodiment of the method when the program is executed by the control unit or the device. In addition to the computer program, such a computer program product can also comprise further parts such as documentation and/or additional components, also hardware components such as a hardware key (dongle etc.) to facilitate access to the software.

Thus, an embodiment of the present application further provides a computer program product with program elements that can be read and executed by a computer unit in order to perform steps of a method according to an embodiment of the present application when the program elements are executed by the computer unit.

A computer readable medium such as a memory stick, a hard-disk or other transportable or permanently-installed carrier can serve to transport and/or to store the executable parts of the computer program product so that these can be read from a processor unit of a control unit or a device. A processor unit can comprise one or more microprocessors or their equivalents.

Thus, an embodiment of the present application further provides a computer-readable medium on which are stored program elements that can be read and executed by a computer unit in order to perform steps of a method according to an embodiment of the present application when the program elements are executed by the computer unit. Further there is provided an electronically readable storage medium, on which a computer program as described above is stored.

Particularly advantageous embodiments and features of the invention are given by the claims, as revealed in the following description. Features of different claim categories may be combined as appropriate to give further embodiments not described herein.

According to a preferred method, the serial radiography image acquisition is a fluoroscopy image acquisition. The preferred method for controlling an X-ray projection imaging device comprises the steps:
  applying preferences for a fluoroscopy image acquisition to the X-ray projection imaging device,
  executing the fluoroscopy image acquisition with the X-ray projection imaging device, wherein a number of data frames (that could here be called "fluoroscopy frames") is recorded at different times during the fluoroscopy image acquisition,
  applying a trigger signal to the X-ray projection imaging device during the fluoroscopy image acquisition,
  generating a snapshot image from a subset of the recorded fluoroscopy frames, wherein this data frame subset is chosen from the recorded fluoroscopy frames based on the trigger signal.

The term "fluoroscopy" generally pertains to the x-ray acquisition of a series of single images (that could theoretically endure for a long time) for observing a dynamic process or just for positioning reasons in an anatomical field of view. Other preferred serial radiography images could be recorded during a (small) time period or comprise only a few images of a high quality (e.g. suitable for a diagnosis) taken during a time period.

According to a preferred method, in the course of the generation of the snapshot image the data frames are combined by using an individual weighting coefficient for each data frame. A weighting coefficient provides information how much a data frame contributes to the snapshot image. In an example, where the data frames comprise digital image data (what is a typical application of the invention), the intensity values of the pixels at identical positions on the data frames could be added, wherein each pixel is multiplied with an individual weighting factor. These weighting factors may be the same for one data frame, however, they could also differ for pixels of one individual data frame. The result could be normalized to provide a snapshot image with a normalized intensity. A suitable formula for describing the generation of a snapshot image S(x,y) from a subset of N data frames Fi(x,y), where coordinates x and y represent the coordinates of the pixels of an image, and weighting coefficients Wi could be:

$$S(x,y)=W_1F_1(x,y)+W_2F_2(x,y)+ \ldots +W_NF_N(x,y) \quad (1)$$

It is preferred that different weighting coefficients are used for at least two data frames, especially for all data frames. For example may it be preferred that the weighting coefficients of data frames "near" the time of the trigger signal have a higher weight coefficient than weighting coefficients of data frames being far earlier or later than the trigger signal. Thus, a set of multiple data frames (e.g. fluoroscopy frames) are differently accumulated to be the input for one or several snapshot images. For example, during the process of snapshot image generation, it is possible to dynamically adapt the influence (weighting) of a single data frame (e.g. a fluoroscopy frame) to the final snapshot image. This means, that one (each) data frame that is used for the snapshot image is provided with an individual weighting factor, e.g. based on its importance concerning time or dose per frame.

It is particularly preferred that at least one weighting coefficient is dynamically adapted during the process of snapshot image generation. Although, it is possible, to dynamically adapt the weighting factor of the data frame at the time the trigger signal is applied (i.e. the data frame nearest this point of time), it is preferred to adjust the weighting factor of other frames used to create the snapshot image, also.

According to a preferred method, in the course of the generation of the snapshot image, a group of data frames recorded before the trigger signal and a group of data frames recorded after the trigger signal are used. Alternatively or additionally the trigger signal can be manually shifted backwards in time such that data frames recorded before the application of the trigger signal are used for generating the snapshot image. This allows the use of data frames that have been recorded before the trigger signal for the generation of the snapshot image. The shift of the trigger signal could e.g. be achieved by manually defining the point in time of the image acquisition where the trigger signal should have been applied.

This has the advantage that the temporal focus of the snapshot image lies at the time of the trigger. However, changes in data acquisition (e.g. higher dose or higher frame rate) are only possible after the trigger signal has been applied. Thus, the above described weighting of the data frames may be very advantageous in combination with this embodiment.

There may be the case that a dynamically weighted averaging (for noise reduction) is already present in the data frames. This can also not be excluded before the trigger signal. Here it is preferred that "raw" data frames (data frames without this averaging) are first saved in a data memory and then being averaged afterwards, wherein these "raw" data frames could then be used for generating the snapshot image.

It is also preferred that there are two data streams of data frames, one stream of raw data frames for snapshot image generation and one stream of processed data frames optimized for displaying or examination.

With this embodiment it is advantageously possible to generate a snapshot image of an event lying before the original trigger signal, e.g. because the reaction time for a surprising event was not fast enough.

According to a preferred method, after a trigger signal is applied and at least for the time where data frames are recorded for generating the snapshot image the image receptor dose per data frame is (dynamically) adapted, and/or the framerate is (dynamically) increased. Both has the advantage that the image quality depending on the specific procedure demands regarding signal-to-noise ratio and time resolution can be optimized.

Additionally or alternatively, the influence of different regions of data frames is (dynamically) adapted to the final snapshot image. This is done wherein the X-ray projection imaging device stays in the mode for serial radiography image acquisition, preferably in the mode for fluoroscopy image acquisition. Thus, in contrast to the state of the art, the acquisition mode is not altered to provide the snapshot image.

Thus, for example, during the process of snapshot image generation, it is possible to dynamically adapt the image receptor dose per image optimizing the image quality depending on the specific procedure demands regarding signal-to-noise ratio and time resolution. Alternatively or additionally during the process of snapshot image generation, it is possible to dynamically increase the framerate optimizing the image quality depending on the specific procedure demands regarding signal-to-noise ratio and time resolution. Also alternatively or additionally during the process of snapshot image generation, it is possible to dynamically adapt the influence of different image regions to the final snapshot image.

It should be noted that the dynamical adaption of the image receptor dose per image is typically achieved by altering preferences of the X-ray projection imaging device. However, this alteration must not exceed the point where the serial radiography image acquisition mode is left. In the case the preferences are altered it is preferred that after the last data frame for the snapshot image is recorded or at least after the snapshot image is generated, the preferences are restored to values present before the application of the trigger signal.

According to a preferred method, during or after the generation of the snapshot image
- intermediate images constructed in the course of this generation are displayed and/or
- the generated snapshot image is displayed and/or
- the original data frames are displayed as images, wherein preferably the generation of the snapshot image is performed in background and/or the data frames are displayed on a primary display while the generation of the snapshot image or the generated snapshot image is displayed on a reference display.

Thus, during the process of snapshot image generation, (i) the constructed intermediate images can be displayed successively within the image stream and/or (ii) the final snapshot image can be displayed or (iii) original fluoroscopy scene is displayed, snapshot generation is performed in background and/or (iv) original fluoroscopy scene is displayed on primary monitor while generation of snapshot image is displayed on reference monitor besides. Here (especially regarding above item (i)) there is preferably applied an automatic periodic trigger signal. This periodic trigger signal could be applied with a preferred frequency lower than 1 Hz, but at least with a frequency such that more than one snapshot is triggered during acquisition time. It is also preferred that a number of snapshots is predefined and the frequency of the trigger signal is calculated such that a similar number of trigger signals is applied during the acquisition period.

The above alternative with "intermediate images" pertains to a method where a snapshot image is produced from intermediate images, wherein these intermediate images are calculated from data frames. These intermediate images could be optimized data frames, e.g. where image-processing techniques like a registration, have been applied. However, these intermediate images could be images from an iteratively generated snapshot image, wherein after each integration of a new data frame an updated snapshot image is generated. The intermediate images are here preferably older snapshot images (snapshot images of preceding iterations). The iterations could be calculated until a predefined number of data frames is reached. For example, in a case where a subset of N=10 data frames should be aligned to one snapshot image. After the integration of data frame 1 the snapshot image will be displayed, after the next iteration, the snapshot image generated from data frames 1 and 2 will be displayed and the last snapshot image will be regarded as intermediate image (and preferably also be displayed) and so on.

According to a preferred method, the trigger signal is generated manually and/or automatically based on predefined parameters and/or automatically based on detected content in a data frame.

Thus, the start of the snapshot image generation can be triggered manually by user interaction, automatically based on parameters or even from automatically detected image content, e.g. port position, catheter location, or contrast agent bolus contrast.

Especially in combination with real-time image analysis, automated triggering of snapshots can simplify the procedure for the user and avoid missing of relevant data frames (e.g. fluoroscopy frames).

According to a preferred method, the generation of a snapshot image is finalized after a predefined number of data frames and/or by user interaction and/or automatically based on detected content in a data frame. Finalizing the snapshot image generation can be done after a parameterizable number of images, by user interaction or also automatically based on the image content (e.g. contrast agent disappeared, noise level dropped under specified threshold).

According to a preferred method, in the data frames used for generating the snapshot image, image-structures are identified being images of the same real object, preferably an organ or other internal structure of a patient, wherein these image structures are registered with another. This has the advantage that (motion-)artifacts are reduced in the snapshot image.

The term "registered" here refers to the technical field of image registration. Image registration is the method of transforming different sets of image data into one coordinate system. Image registration is very advantageous in order to be able to compare or integrate the data obtained from different data frames.

In a preferred system according to the invention, components of the system are part of a data-network, wherein preferably the network (in particular providing communication with the image generation unit) and an X-ray imaging device (which provides the data frames) are in data-communication with each other, wherein the network preferably comprises parts of the internet and/or a cloud-based computing system, wherein preferably the image generation unit is realized in this cloud-based computing system. For example, the components of the system are part of a network, wherein preferably the network and a medical imaging system which provides the image data are in communication with each other. Such a networked solution could be implemented via an internet platform and/or in a cloud-based computing system.

The method may also include elements of "cloud computing". In the technical field of "cloud computing", an IT infrastructure is provided over a network, e.g. a storage space or processing power and/or application software. The communication between the user and the "cloud" is achieved by means of data interfaces and/or data transmission protocols.

In the context of "cloud computing", in a preferred embodiment of the method according to the invention, provision of data via a data channel (for example a network) to a "cloud" takes place. This "cloud" includes a (remote) computing system, e.g. a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System). Preferably, the computing system of the "cloud", the network and the X-ray projection imaging system constitute a network in terms of data technology. The method can be realized by means of a command constellation in the network. The data or results calculated in the cloud are preferably sent back over a data channel (e.g., over a network) to the user's local computer. For example, the data of the image acquisition provided is processed by a computer system of a hospital according to the method according to the invention, and the results of this processing are sent back to the user by means of a RIS or PACS.

Within the scope of a preferred embodiment of the system according to the invention, the abovementioned units (data interface, . . . ) Are present on the "cloud" side. A preferred system further comprises, a local computing unit connected to the device via a data channel (e.g., a network, particularly configured as RIS or PACS). The local computing unit includes at least one data receiving interface to receive data. Moreover, it is preferred if the local computer additionally has a transmission interface in order to send data to the device.

One important advantage of at least one embodiment of the invention is that the snapshot image can be used to replace a single spot image, which in state-of-the-art systems for technical reasons requires a higher dose compared to a fluoroscopy derived image, but the higher dose may not be required for clinical reasons. This offers a potential for patient dose saving.

In FIG. 1, the time of interruption of a fluoroscopy acquisition is outlined by using two common examples. This has already been explained above in the introducing part.

Figure 2:
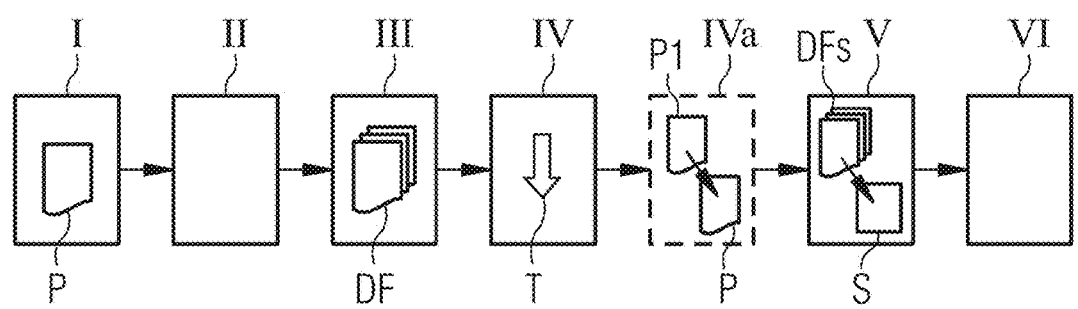
FIG. 2 shows a block diagram of the process flow of a preferred method according to an embodiment of the invention.
Figure 3:
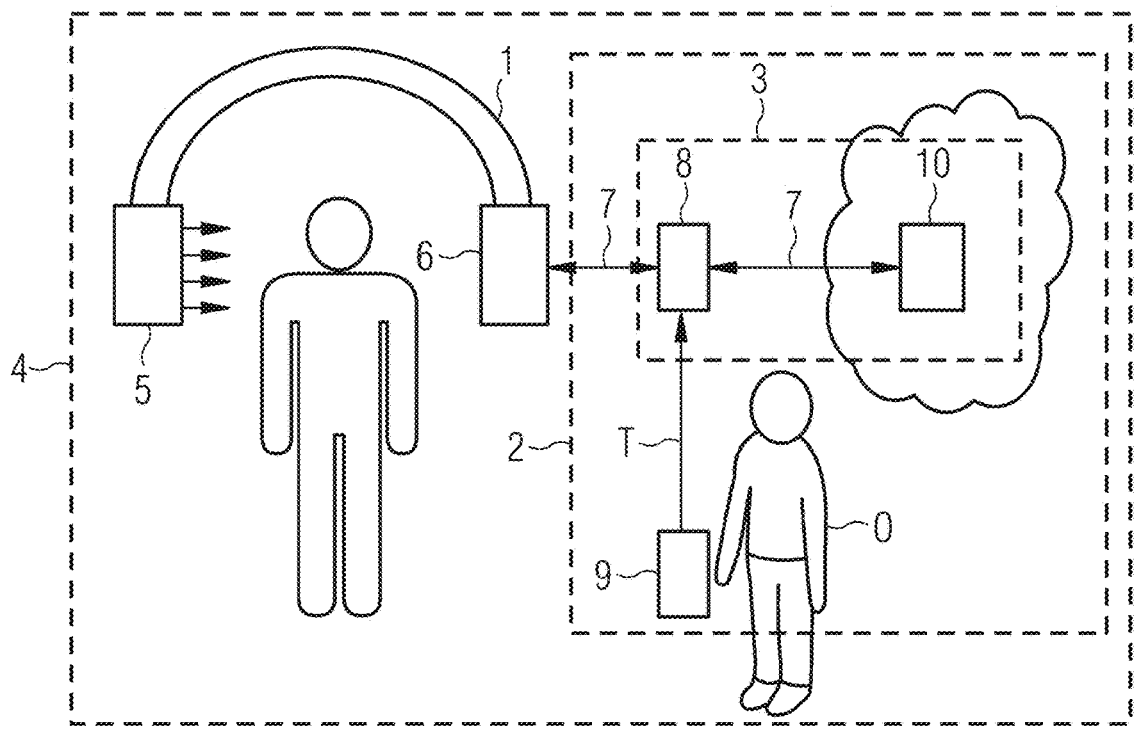
FIG. 3 shows a preferred X-ray projection imaging system with a control unit based on a preferred system according to an embodiment of the invention.

FIG. 2 shows a block diagram of the process flow of a preferred method according to an embodiment of the invention for controlling an X-ray projection imaging device 1 (see. e.g. FIG. 3).

In step I, preferences P for a serial radiography image acquisition, in this example a fluoroscopy acquisition, are applied to the X-ray projection imaging device 1. By setting these preferences, the X-ray projection imaging device will be set into fluoroscopy mode.

In step II, the fluoroscopy image acquisition with the X-ray projection imaging device 1 is started.

In step III, data frames DF are recorded at different times during the fluoroscopy image acquisition.

In step IV, a trigger signal T is applied to the X-ray projection imaging device 1 during the fluoroscopy image acquisition. This trigger signal T may be generated automatically, however, in this example we assume, that this trigger signal T is provided manually by an operator.

In optional step IVa, the preferences P of the X-ray projection imaging device are changed to an amended preference set P1 without leaving fluoroscopy mode. For example, the framerate is temporally increased. In this case, the original preferences P should be established again at least after the snapshot image generation.

In step V, a snapshot image S is generated from a subset of the recorded data frames DF based on the trigger signal T. For example, the data frame subset DFs can be combined by using an individual weighting coefficient for each data frame DF. The generation of the snapshot image S is finalized after a predefined number of data frames DF.

In step VI, the generated snapshot image S is displayed.

FIG. 3 shows a preferred X-ray projection imaging system 4 with an X-ray projection imaging device 1 and a control unit 2 based on a preferred system 3 according to an embodiment of the invention. Here the system is not designed in one housing, but realized as network solution. Shown is a scene, where a fluoroscopy acquisition is done.

A fluoroscopy of a person is made with an X-ray projection imaging device 1 comprising an X-ray source 5 and an X-ray detector 6. This X-ray projection imaging device 1 is connected via a data connection 7 with a data interface 8. The data connection 7 here also represents a data network 7.

This data interface 8 (e.g. a biserial data interface) is designed for read and write data and is part of the system 3. The data interface 8 facilitates the application of preferences P for a fluoroscopy image acquisition to the X-ray projection imaging device 1, as well as the starting of an execution of a fluoroscopy image acquisition with the X-ray projection imaging device 1, the receiving of a number of data frames DF and the application of a trigger signal T to the X-ray projection imaging device 1. The trigger signal T is given by an operator O via a trigger input unit 9.

The system 3 also comprises an image-generation unit 10 designed for generating a snapshot image S from a subset of the data frames DF, wherein this data frame subset DFs is chosen from the recorded data frames DF based on the trigger signal T (see e.g. FIG. 2). In this example, the image-generation unit 10 is contacted via another data connection 7 (e.g. the internet) and is part of a cloud-based computing system 11 providing the image-generation unit 10 as a cloud-based service.

Here, the trigger input device 9 is not part of the system 3, but of the control unit 2. However, this solution is only one possibility.

Figure 4:
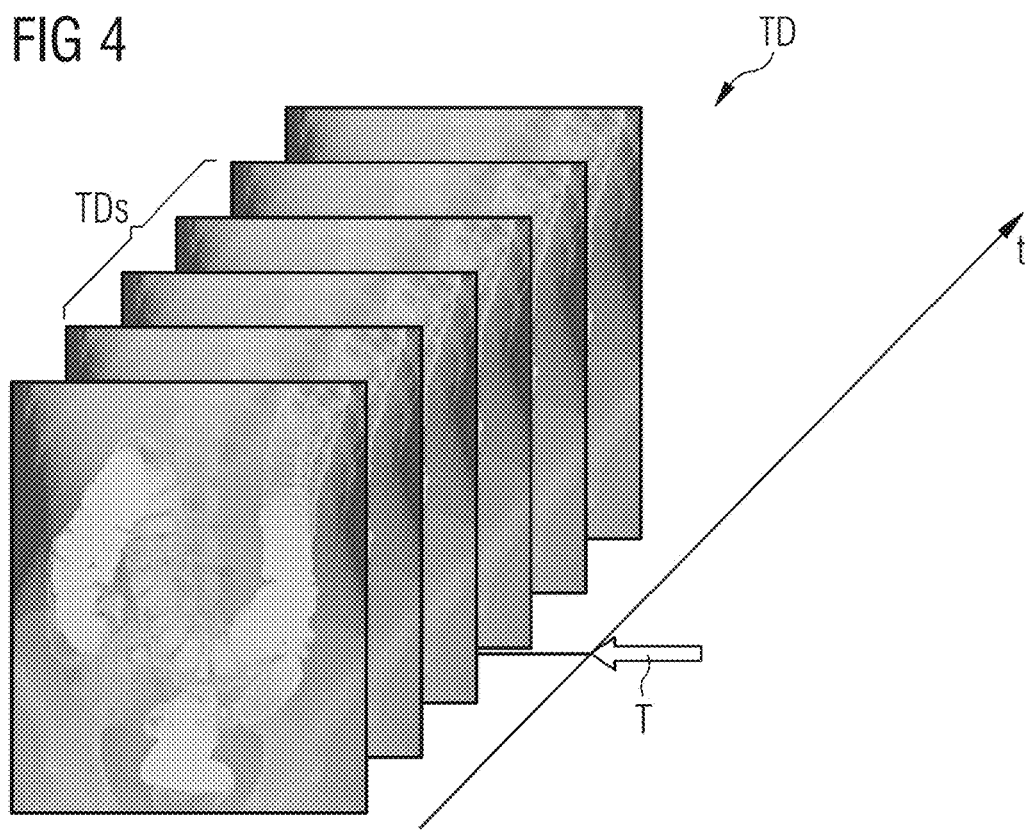
FIG. 4 clarifies the forming of a data frame subset.

FIG. 4 clarifies the forming of a data frame subset DFs for generation of a snapshot image S (see also FIG. 2). In the course of a serial radiography image acquisition data frames (here images) are recorded at different times. The passing time t is indicated by the arrow leading from bottom to top. At a certain point of time, a trigger signal T is applied. Based on this trigger signal T (i.e. the point of time of this trigger signal T), a data frame subset DFs is chosen. This data frame subset DFs could be chosen by selecting a predefined number of data frames DF starting from the trigger signal T. In this example, there is a number of four data frames DF predefined and there are two data frames DF chosen for the data frame subset DFs that have been recorded (and saved in a memory) before the trigger signal T and two data frames DF that have been recorded after the trigger signal T.

For generating a snapshot image S that accurately represents the situation at the time the trigger signal T was applied, the data frames could be linearly combined (e.g. by adding the intensities of corresponding pixels of different data frames DF of the data frame subset DFs), including a higher weighting of the both data frames DF in the (temporal) middle of the data frame subset DFs.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other steps or elements. The mention of a "unit" or a "device" does not preclude the use of more than one unit or device.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for controlling an X-ray projection imaging device, comprising:
    applying preferences for a serial radiography image acquisition to the X-ray projection imaging device;
    executing the serial radiography image acquisition with the X-ray projection imaging device;
    recording data frames at different times during the serial radiography image acquisition;

applying a trigger signal to the X-ray projection imaging device during the serial radiography image acquisition; and generating a snapshot image from a subset of the data frames, wherein the subset is chosen from the data frames recorded based on the trigger signal.

2. A method of claim 1, wherein the serial radiography image acquisition is a fluoroscopy image acquisition.

3. The method of claim 1, wherein in the generating of the snapshot image, the data frames are combined by using an individual weighting coefficient for each data frame of the data frames.

4. The method of claim 1, wherein a group of the data frames recorded before the trigger signal and a group of the data frames recorded after the trigger signal are used in the generating of the snapshot image.

5. The method of claim 1, after a trigger signal is applied and at least for the time where the data frames are recorded for generating of the snapshot image, at least one of:
an image receptor dose per data frame is adapted,
a framerate is increased, and
an influence of different regions of the data frames is adapted to a final snapshot image,
wherein the X-ray projection imaging device is configured to stay in a mode for serial radiography image acquisition.

6. The method of claim 1, wherein during or after the generating of the snapshot image, at least one of:
intermediate images constructed in the generating are displayed,
the snapshot image generated is displayed, and
original data frames are displayed as images.

7. The method of claim 1, wherein the trigger signal is generated at least one of manually, automatically based on defined parameters, and automatically based on detected content in a data frame.

8. The method of claim 1, wherein the generating of the snapshot image is finalized at least one of:
after a number of data frames,
by user interaction, and
automatically based on detected content in a data frame.

9. The method of claim 1, wherein in the data frames used for generating the snapshot image, image-structures are identified being images of a same real object, the image structures each being registered.

10. A system for controlling an X-ray projection imaging device, comprising:
a data interface, designed to apply preferences for a serial radiography image acquisition to the X-ray projection imaging device;
a second data interface, designed to start an execution of a serial radiography image acquisition with the X-ray projection imaging device;
a third data interface, designed to receive a number of data frames recorded at different times during the serial radiography image acquisition;
a fourth data interface, designed to apply a trigger signal to the X-ray projection imaging device during the serial radiography image acquisition; and
an image-generation unit, designed to generate a snapshot image from a subset of the data frames, wherein the subset being chosen from the data frames recorded based on the trigger signal.

11. The system of claim 10, wherein the data interfaces and the image-generation unit of the system are part of a data-network, the data network and a x-ray imaging device, configured to provide the data frames, being in data-communication, wherein the data network comprises at least one of parts of the internet and a cloud-based computing system.

12. A control unit for controlling an X-ray projection imaging device comprising the system of claim 10.

13. An X-ray projection imaging system, comprising:
a X-ray projection imaging device; and
the control unit of claim 12.

14. A non-transitory computer program product comprising a computer program, directly loadable into a system or a control unit for an x-ray projection imaging device, including program elements for performing the method of claim 1 when the computer program is executed by the system or the control unit.

15. A non-transitory computer-readable medium storing program elements, readable and executable by a computer unit to perform the method of claim 1 when the program elements are executed by the computer unit.

16. A control unit for controlling an X-ray projection imaging device comprising the system of claim 11.

17. The X-ray projection imaging system of claim 13, wherein the X-ray projection imaging device is a radiography system or fluoroscopy system including a central processing unit or a computer for evaluation of image data.

18. The method of claim 1, wherein different weighting coefficients are used for at least two of the data frames, and wherein at least one weighting coefficient is dynamically adapted during the generating of the snapshot image.

19. The method of claim 4, the trigger signal is manually shiftable backwards in time such that a group of the data frames recorded before the applying of the trigger signal are used for the generating of the snapshot image.

20. The method of claim 6, wherein at least one of
the generating of the snapshot image is performed in background and
the data frames are displayed on a primary display while the generating of the snapshot image or the snapshot image generated is displayed on a reference display.

21. The method of claim 9, wherein in the data frames used for generating the snapshot image, an organ or other internal structure of a patient are identified being images of a same real object.

22. A system for controlling an X-ray projection imaging device, comprising:
a data interface, designed to
apply preferences for a serial radiography image acquisition to the X-ray projection imaging device,
start an execution of a serial radiography image acquisition with the X-ray projection imaging device,
receive a number of data frames recorded at different times during the serial radiography image acquisition, and
apply a trigger signal to the X-ray projection imaging device during the serial radiography image acquisition; and
an image-generation unit, designed to generate a snapshot image from a subset of the data frames, wherein the subset being chosen from the data frames recorded based on the trigger signal.

23. The system of claim 22, wherein the data interface and the image-generation unit of the system are part of a data-network, the data network and a x-ray imaging device, configured to provide the data frames, being in data-communication, wherein the data network comprises at least one of parts of the internet and a cloud-based computing system.

24. A control unit for controlling an X-ray projection imaging device comprising the system of claim 22.

25. An X-ray projection imaging system, comprising:
a X-ray projection imaging device; and
the control unit of claim 24.

* * * * *